United States Patent [19]

Downie et al.

[11] 4,216,776
[45] Aug. 12, 1980

[54] DISPOSABLE AORTIC PERFORATOR

[75] Inventors: David E. Downie, Lafayette; Robert J. Harvey, Danville; John R. Rueff, Concord, all of Calif.

[73] Assignee: Thoratec Laboratories Corporation, Berkeley, Calif.

[21] Appl. No.: 907,761

[22] Filed: May 19, 1978

[51] Int. Cl.² .............................................. A61B 17/32
[52] U.S. Cl. .................................................... 128/305
[58] Field of Search ............... 128/305, 2 B, 305.3, 128/751, 753, 754; 30/241

[56] References Cited

U.S. PATENT DOCUMENTS

| | | | |
|---|---|---|---|
| 3,104,666 | 9/1963 | Hale et al. | 128/305.3 |
| 3,776,237 | 12/1973 | Hill et al. | 128/305 |
| 4,018,228 | 4/1977 | Goosen | 30/241 X |
| 4,099,529 | 7/1978 | Peyman | 128/305 |

*Primary Examiner*—Robert W. Michell
*Assistant Examiner*—Michael H. Thaler
*Attorney, Agent, or Firm*—Lothrop & West

[57] ABSTRACT

A disposable aortic perforator has an elongated stem with an exterior stem surface circular-cylindrical about a longitudinal axis and extending between a far end and a near end. A coaxial disc having an exterior circumferential cylindrical disc surface of a first predetermined diameter is separated from the remainder of the stem by an intervening groove leaving an axial shank therebetween. The coaxial disc has a near surface on said disc normal to the axis and meeting the disc peripheral surface substantially at a right angle to form a blunt outside corner that is a non-cutting edge. An elongated tube is telescoped over the stem and is slidable a predetermined distance, about one-third of an inch, on the stem. The tube has an interior, circumferential cylindrical or tube surface of a second predetermined diameter about 0.0002 inches larger than the first predetermined diameter of the stem. An annular surface at the far end of the tube and normal to the axis meets the interior tube surface substantially at a right angle and forms a blunt inside corner that is a non-cutting edge. A cross bar normal to the axis engages the stem and preferably is disposed in a jacket slidable on or with respect to the tube. A spring is interposed between the stem and the tube for urging the tube axially away from the disc, the motion being limited by interengagement of slots in the tube with the cross bar.

8 Claims, 7 Drawing Figures

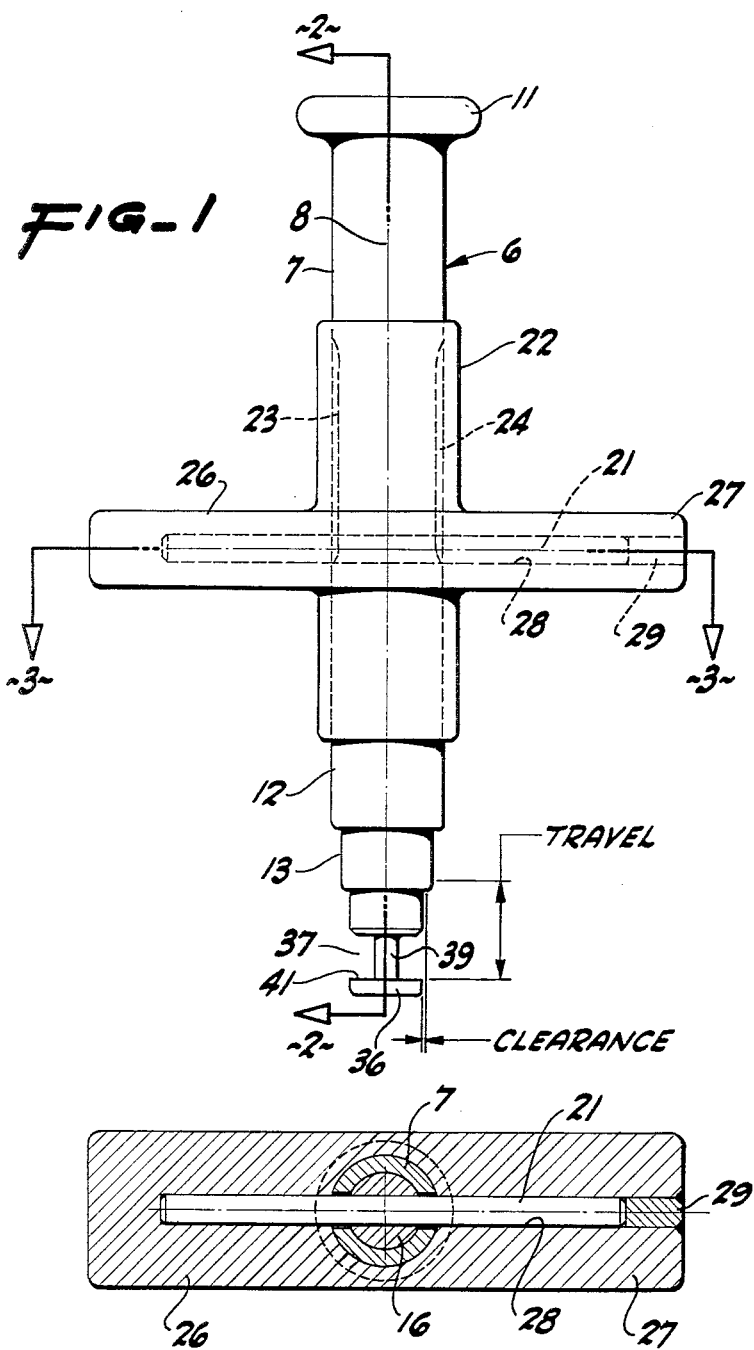
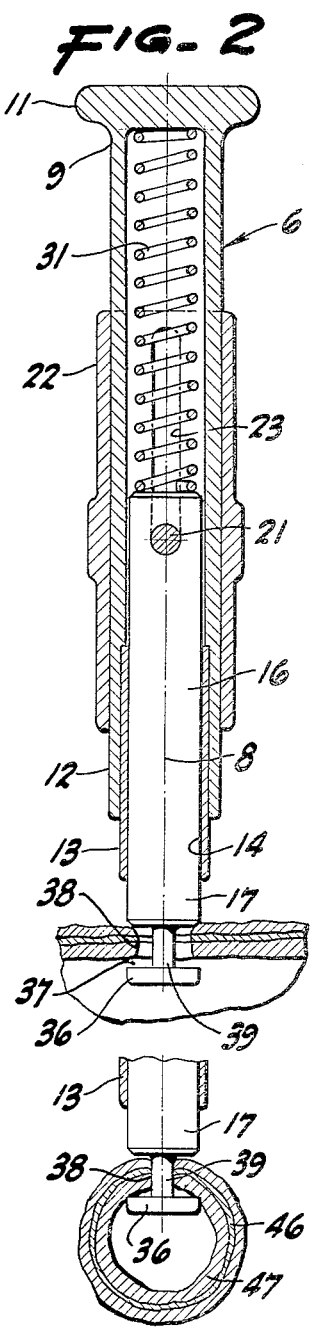

DISPOSABLE AORTIC PERFORATOR

BRIEF SUMMARY OF THE INVENTION

Especially for use in aortocoronary or like bypass operations in which a blood vessel such as a prepared vein is attached to the aorta around an opening made in the aortic wall, various cutting devices have been proposed for making the aortic perforation. It has been found that the somewhat elastic, fibrous layer or adventitia near the exterior of the aorta makes it difficult to provide the hole easily, consistently and quickly. In the present instance there is provided a device which tends to sever and position the normal tissue accompanying the adventitia in a satisfactory way, but particularly is arranged to dispose and stretch the adventitia sufficiently to that the adventitia fails generally in tension rather than shear. This is accomplished by particular right-angle, blunt configurations of closely spaced disc and tube portions of the device having an amount of relative travel effective to afford tension failure and results in a superior provision of the necessary perforation.

BRIEF DESCRIPTION OF THE SEVERAL VIEWS OF THE DRAWINGS

FIG. 1 is a side elevation of an aortic perforator constructed pursuant to the invention and shown in normal position.

FIG. 2 is a view in cross-section, the plane of which is indicated by the line 2—2 of FIG. 1, and with the device in position for use with an aortic wall.

FIG. 3 is a cross-section, the plane of which is indicated by the line 3—3 of FIG. 1.

FIG. 4 is a cross-section similar to FIG. 2 but showing only the lower portion of the device and disposed at right angles to the view of FIG. 2.

Figure 5:
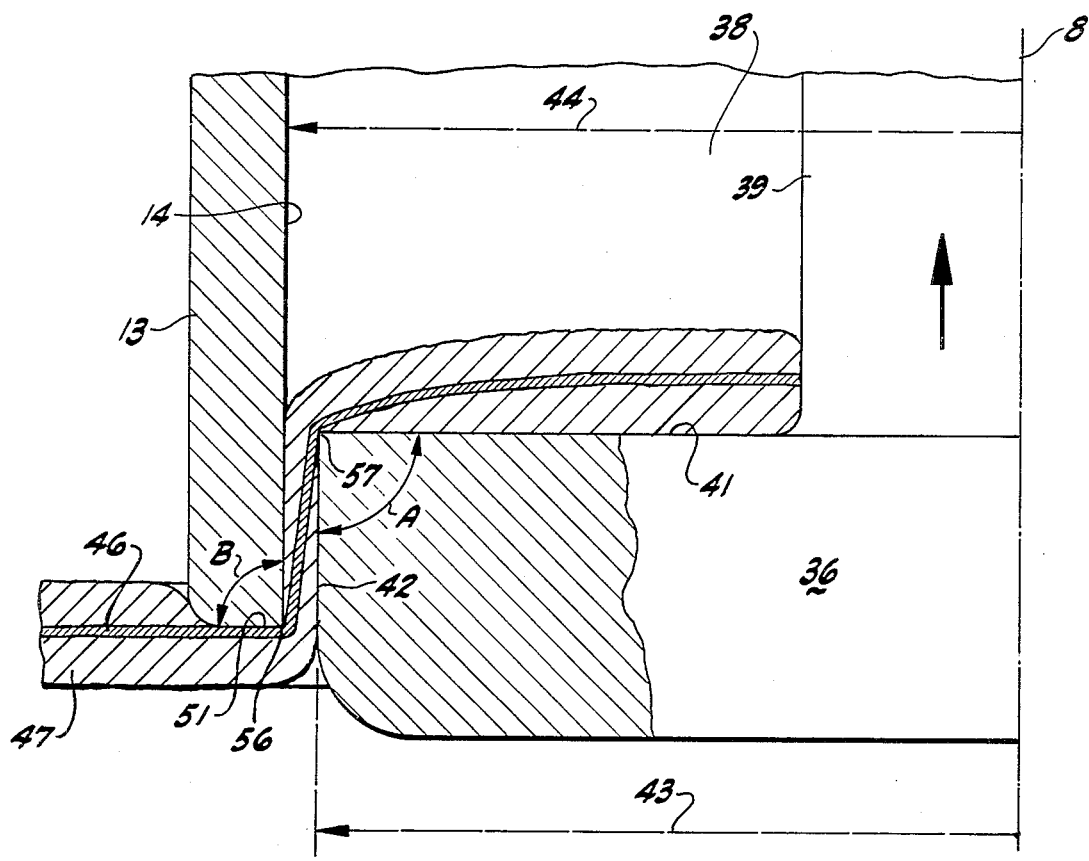
FIG. 5 is an enlarged detail of the lower end of the device shown in use in providing a perforation, much of the surroundings being broken away.

The drawings indicate general proportions but are not exactly to scale.

DETAILED DESCRIPTION

Particularly for use in bypass operations, it is necessary to provide an opening through the wall of the aorta. The wall is a composite structure made up of internal tissue and an enveloping layer principally of a relatively elastic, fibrous material referred to as the advantitia. There is sometimes an overlying layer of substantial fat. Because of the heterogeneous makeup of the aorta wall, it is not always easy to provide an appropriate aperture therethrough. Various devices have been made available for that purpose. Among them are those shown in the patents to Hoffman U.S. Pat. No. 1,867,624, to Hale et al. U.S. Pat. No. 3,104,666, to Hill et al. U.S. Pat. No. 3,776,237, and to Goosen U.S. Pat. No. 4,018,228. While all of those devices are well known, it is still desired to provide a device which has improved characteristics in that it deals particularly well with the advantitia and with any fatty layer, can be made easily and inexpensively enough so that it can be utilized but once or a few times and then discarded, is likely to afford a substantially uniform response when operated by the surgeon, and requires a small, steady amount of force to perforate the aorta, including the adventitia, and to deal properly with any fatty layer. It is also advantageous in that the perforation provided has characteristics consistent with accepted surgical practice. The tool leaves an appropriate marginal configuration around the opening for vein attachment and for smooth blood flow.

The instant arrangement can be made almost entirely of surgical steel and comparable materials for long-term and permanent use with repeated sterilization. But it has been deemed advantageous in many instances to make the device of somewhat less expensive materials. While some close tolerances are used, there are no sharp cutting edges, so that only medium grade steels can be used and much of the device can be of suitable plastic. After an initial sterilization and use, it is economically feasible to discard the device.

In a representative form, the structure has been successfully incorporated as shown herein. There is provided a tube 6 made of metal, or if the device is to be disposable then conveniently made of sterilizable plastic material. The tube has a generally circular-cylindrical outside surface 7 coaxial with a longitudinal axis 8. The tube is generally closed at its near or upper end 9 and is provided with a thumb disc 11. At its far or lower end 12, the tube 6 may be unitary, but if of plastic preferably has a metal, inserted tube 13 long with respect to its internal diameter to provide a stable bearing. The tube 13 is smaller in outside diameter than the outside diameter of the tube 6. The tube 13 has an interior circular-cylindrical surface 14 coaxial with the axis 8 and smaller than the inside diameter of the tube 6.

Designed to move axially within and relative to the tubes 6 and 13 is a coaxial stem 16 having a circular-cylindrical outside surface 17 that is only slightly smaller in diameter than the inside surface 14 of the tube 13. The two parts are freely slidable with respect to each other but have a very minimum of radial or transverse play. The upper or near end of the stem 16 is joined by a through rod 21 to an outer, preferably plastic, jacket 22 freely slidable on the exterior of the tube 6 and preferably overlying axial slots 23 and 24 through which the rod 21 passes. The slot ends serve as limits on the relative axial movement of the tube and the stem and allow a travel of the disc 36 within the tube 13 of the order of one-third of an inch. Conveniently, the jacket is integrally formed with arms 26 and 27 encasing the rod 21. Preferably, the rod is inserted originally through an opening 28 in one arm end, and the opening is then provided with a plug 29. A spring 31 is interposed between the upper end of the stem 16 and the interior, closed end of the tube, so as to urge the stem in a direction out of the tube.

The foregoing portion of the structure is particularly augmented and improved by the provision on the far or lower end of the stem 16 of a circular, terminal disc 36 coaxial with the axis 8 and separated from the remainder of the stem by an intervening groove 37 leaving a connecting shank 39 therebetween. Particularly as shown enlarged in FIG. 5, the shank 39 merges with the terminal disc 36 to leave a near surface 41 normal to the axis 8. The surface 41 extends to and merges with an outer, circular-cylindrical surface 42 on the disc 36 and having a first predetermined diameter 43. The surfaces 41 and 42 bluntly and not sharply intersect each other substantially at a right angle A and form a non-cutting edge. The lower or far portion of the tube 13 has the inner, circular-cylindrical surface 14 of a second predetermined diameter 44 carefully related to the predetermined diameter 43. In the ordinarily sized device, the difference between the two diameters 43 and 44 is approximately 0.0002 inches. This difference or annular space is approximately that required in most practice to accommodate the adventitia 46 in the ordinary aortic wall 47 and does not accommodate but rather excludes much of the fatty layer on the aortic wall.

Furthermore, the tube 13 is not only bounded by the interior circular-cylindrical wall or surface 14, but likewise as its far or lower end is finished by an annular wall 51 normal to the axis 8 and bluntly and not sharply joining the interior wall 14 at a right angle B and form a non-cutting edge. The arrangement is such that while the disc 36 can be axially positioned substantially beyond the end of the tube 13, as shown in FIG. 2, nevertheless the disc can also occupy a position well within the interior of the tube 13 as shown in FIG. 5. The distance that the disc intrudes axially into the interior portion of the tube 13 is somewhat variable, but is more than simply a preliminary entry, an effective value being about one-third of an inch, this being a stroke long enough to cause the adventitia fibers to fail in tension.

In the customary use of this device, the aorta is preferably prepared for the use of the structure in the customary way by preliminarily making a single, linear incision 38 through all of the layers of the aorta in a direction at the discretion of the surgeon and of a length slightly less than the outside diameter of the disc 36. When that has been done, the perforator in its extended position, as shown in FIGS. 1 and 2, is maneuvered by the surgeon so that the disc 36 is passed through the incision just made in the aortic wall, the incision being sufficiently stretched to admit of the disc. Since neither the tube nor the disc has a cutting edge, there is no chance of an inadvertent nick or cut in the aorta during this positioning. The perforator is then maneuvered into the position illustrated in FIG. 4, the elastic walls of the incision lying closely on opposite sides of the shank 39 and ending substantially within the diameter 44.

The surgeon then, with his fingers hooked under the arms 26 and 27 and his thumb on the end disc 11, presses the tube 6 so that its near end approaches the arms 26 and 27. The effect is to move the tube 13 and the disc 36 to approach each other and closely to engage the opposite surfaces of the aorta and rather readily to cut through the interior tissue and to exclude much of the exterior fatty tissues. A little fatty tissue is not detrimental, but the dimension of about 0.0002 is held because a thick layer of fat between the tube 13 and the stem 16 may cause the parts to jam.

The adventitia 46, however, is not as readily handled. Rather, the adventitia tends to bend sharply over the inner edge 56 or corner of the tube and rather sharply, although perhaps not quite to such a great extent, also to bend over the outer edge 57 or corner on the disc 36. The blunt edges of the tool form induced abrupt bends in the adventitia tending to hold a restricted band of the adventitia generally in a tubular position and in an axial orientation without substantial slipping. As the tube 13 telescopes farther and farther over the disc 36, the adventitia is stretched until the adventitia fails in tension all around the periphery of the disc 36. The desired opening has thus been made.

Two dimensions are important to the effective operation of the aortic perforator. The distance that the disc 36 intrudes axially into the interior portion of the tube 13 is important in that it produces axial parting of the adventitia by separating in tension, a distance as established in practice of about one-third of an inch. The difference between the disc diameter 43 and the tube diameter 44 is important in that it must be small enough to prevent the entering of excess fatty tissue into the annular space between the disc 36 and the tube 13, a difference established in practice of about 0.0002 inches.

Figure 6:
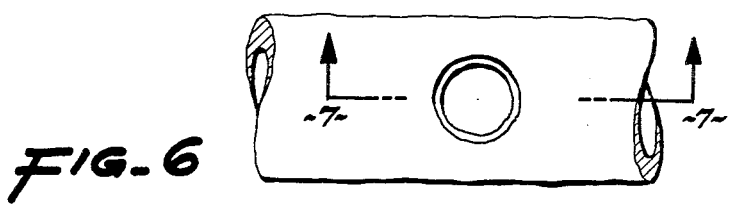
FIG. 6 is a plan of a section of aorta with a perforation therein as produced by the present device.
Figure 7:
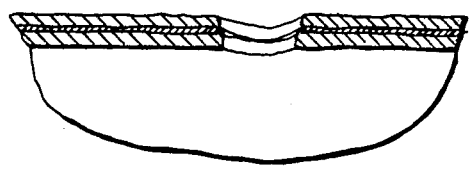
FIG. 7 is a cross-section, the plane of which is indicated by the line 7—7 of FIG. 6.

Following the production of the desired opening, the surgeon removes the device with the severed aortic material captured therein and relaxes his previously uniform clasp on the tool. The spring 31 then restores the parts substantially to the position shown in FIG. 2 and the removed material is dislodged from the again-extended tool. The device having been removed, the aorta is left undisturbed but with a predetermined aperture in the wall thereof. Since the adventitia is somewhat elastic, the remaining portion tends to contract and thus to enlarge slightly the outer periphery of the perforation just made, as shown in FIGS. 6 and 7. This configuration of the perforation or orifice is advantageous not only in attaching a relatively circular vein end in registry with the opening, but also in affording a good flow path for the blood from the aorta into the newly attached vein.

The device as removed can be immediately discarded or can be stripped of the portion of the aortic wall just removed and can be reutilized on the same patient. The tool is generally inexpensive enough to be discarded after use on but one patient, although can be resterilized and used on other patients if desired.

It has been found in practice that with this arrangement the force required from the surgeon is relatively uniform, steady and low, so that the job can be effectively done with one hand and without undue jerking or displacement. While the right-angled edges do some separation of normal tissue, they do not necessarily cut or shear the adventitia, but rather cause the adventitia to fail in tension. The absence of sharp edges is an advantage not only in the original production of the tool, since sharpening is not required, but more particularly in the use of the tool, since the absence of sharp edges precludes any inadvertent or accidental nicks or cuts on the aorta or on any of the adjacent tissues.

We claim:

1. A disposable aortic perforator comprising an elongated stem having an exterior stem surface circular-cylindrical about a longitudinal axis and extending between a far end and a near end; a coaxial disc having an exterior, circumferential cylindrical disc surface of a first predetermined diameter; means defining a near surface on said disc normal to said axis and meeting said cylindrical disc surface substantially at a right angle forming an outside corner supportive of a length of adventitia disposed substantially in a right-angle configuration abutting against said near surface and said disc surface; an axial shank connecting said disc and said far end of said stem; and elongated tube telescoped over and axially movable on said stem, said tube having an interior, circumferential cylindrical tube surface disposed to telescope over said exterior cylindrical disc and of a second predetermined diameter slightly larger than said first predetermined diameter and defining an annular clearance space of predetermined radial dimension at least as great as the thickness of a length of said adventitia disposed between said interior tube surface and said exterior disc surface; means defining an annular surface on said far end of said tube normal to said axis and meeting said interior tube surface surface substantially at a right angle and forming an inside corner supportive of said length of adventitia disposed substantially in a right-angle configuration abutting against said annular surface and said interior tube surface; a cross bar normal to said axis, means for fixing said cross bar in said stem; a spring for urging said tube axially away from said disc; and means for limiting axial movement of said tube relative to said stem.

2. In an aortic perforator including a tube cylindrical about an axis with a near end and a far end and having a cylindrical inner wall surface of a predetermined inside diameter, said far end being an annulus in a plane normal to said axis, a stem movable within said tube, said stem having a near end and a far end having a reduced shank adjacent said far end, a terminal disc on said shank, said disc having a cylindrical outer wall surface of a predetermined outside diameter to leave a predetermined annular space between said outer wall surface of said disc and said inner wall surface of said tube, said space having a radial dimension at least as great as the thickness of a length of adventitia, means for urging said stem to move axially in said tube, and means for limiting the axial movement of said stem in said tube, the improvement comprising means defining substantially a right-angle outer gripping edge on the near end of said disc and forming a corner supportive of said length of adventitia disposed substantially in a right-angle configuration abutting against said outer gripping edge, and means defining substantially a right-angle inner gripping edge supportive of said length of adventitia and disposed on the far end of said tube positioned to cooperate with said outer gripping edge to place adventitial material therebetween in tension.

3. A device as in claim 2 in which said tube cylindrical inner wall surface and said disc cylindrical outer wall surface have a predetermined annular clearance therebetween of approximately 0.0002 inches.

4. A device as in claim 2 in which said limiting means allows movement of said disc into said tube an axial distance sufficient to cause failure in tension of aortic adventitia overlying and extending axially between said right-angle outer gripping edge and said right-angle inner gripping edge.

5. A device as in claim 4 in which said distance is about one-third of an inch.

6. A device as in claim 5 in which said tube and said stem have a radial sliding engagement of about one-third of an inch throughout which said predetermined diametrical clearance of 0.0002 inches is substantially maintained.

7. A device as in claim 2 in which said tube and said disc have a diametrical clearance between them sufficient to receive aortic adventitia and to exclude substantial adjacent aortic fatty tissue.

8. A device as in claim 2 in which all surfaces of said tube and said disc in contact with aortic tissue, including the adventitia, are blunt.

* * * * *